(12) United States Patent
De Cicco et al.

(10) Patent No.: US 11,576,652 B2
(45) Date of Patent: Feb. 14, 2023

(54) INTRALUMINAL IMAGING DEVICES WITH MULTIPLE CENTER FREQUENCIES

(71) Applicant: KONINKLIJKE PHILIPS N.V., Eindhoven (NL)

(72) Inventors: Dino De Cicco, Carlsbad, CA (US); Eric Khairy, San Diego, CA (US); David Goodman, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 769 days.

(21) Appl. No.: 16/048,121

(22) Filed: Jul. 27, 2018

(65) Prior Publication Data

US 2019/0029642 A1 Jan. 31, 2019

Related U.S. Application Data

(60) Provisional application No. 62/538,640, filed on Jul. 28, 2017.

(51) Int. Cl.
*A61B 8/00* (2006.01)
*A61B 8/12* (2006.01)
(Continued)

(52) U.S. Cl.
CPC .............. *A61B 8/4461* (2013.01); *A61B 8/06* (2013.01); *A61B 8/085* (2013.01); *A61B 8/0891* (2013.01); *A61B 8/12* (2013.01); *A61B 8/445* (2013.01); *A61B 8/4477* (2013.01); *A61B 8/4494* (2013.01); *A61B 8/488* (2013.01); *A61B 8/5246* (2013.01); *A61B 5/0084* (2013.01); *A61B 6/12* (2013.01); *A61B 6/5247* (2013.01); *A61B 8/4281* (2013.01); *A61B 8/5238* (2013.01);
(Continued)

(58) Field of Classification Search
None
See application file for complete search history.

(56) References Cited

U.S. PATENT DOCUMENTS 6,641,540 B2 11/2003 Fleischman
7,717,851 B2 5/2010 Karasawa
(Continued)

FOREIGN PATENT DOCUMENTS

CN 1257695 A 6/2000
CN 104605892 A 5/2015
(Continued)

OTHER PUBLICATIONS https://www.merriam-webster.com/dictionary/parallel (last visited Jun. 21, 2022).*

*Primary Examiner* — Joel F Brutus

(57) ABSTRACT

Intravascular ultrasound (IVUS) imaging devices, systems, and method are provided. In one embodiment, an IVUS imaging device includes a flexible elongate member configured to be positioned within a lumen of a patient, the flexible elongate member comprising a proximal portion and a distal portion; and an imaging assembly disposed at the distal portion of the flexible elongate member. The imaging assembly includes a first ultrasound transducer operating at a first center frequency; and a second ultrasound transducer operating at a second center frequency different from the first center frequency.

12 Claims, 7 Drawing Sheets

(51) Int. Cl.
*A61B 8/08* (2006.01)
*A61B 8/06* (2006.01)
A61B 5/00 (2006.01)
A61B 6/12 (2006.01)
A61B 6/00 (2006.01)

(52) U.S. Cl.
CPC ............... *G06T 2207/10132* (2013.01); *G06T 2207/30101* (2013.01)

(56) References Cited

U.S. PATENT DOCUMENTS

| | | | |
|---|---|---|---|
| 7,846,101 B2 | 12/2010 | Eberle et al. | |
| 2012/0123271 A1* | 5/2012 | Cai | A61B 8/463 600/454 |
| 2013/0303910 A1* | 11/2013 | Hubbard | A61B 8/06 600/443 |
| 2014/0187964 A1 | 7/2014 | Corl et al. | |
| 2014/0236011 A1 | 8/2014 | Fan et al. | |
| 2014/0276079 A1 | 9/2014 | Yamagata et al. | |
| 2015/0305716 A1* | 10/2015 | Rice | A61B 8/4461 600/445 |

FOREIGN PATENT DOCUMENTS

| | | |
|---|---|---|
| WO | 2006113857 A1 | 10/2006 |
| WO | 2013181194 A1 | 12/2013 |

\* cited by examiner

INTRALUMINAL IMAGING DEVICES WITH MULTIPLE CENTER FREQUENCIES

TECHNICAL FIELD

The present disclosure relates generally to intravascular ultrasound (IVUS) imaging and, in particular, to an imaging element of an intravascular imaging device. For example, the imaging element can include multiple ultrasound transducers operating at different center frequencies.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters and rotational IVUS catheters are two types of IVUS devices commonly used today. Both types of the IVUS devices are capable of imaging around the circumference of the vasculature. For rotational IVUS devices, a side looking transducer disposed in a distal portion of a flexible elongate member scans the vasculature as it rotates around a longitudinal axis of the flexible elongate member. The solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation).

Traditionally, an IVUS device, whether being rotation or solid-state, is equipped with an ultrasound transducer or an array of ultrasound transducers operating at a single center frequency. Because an ultrasound transducer operating at a higher center frequency has higher spatial resolution but less depth of penetration than an ultrasound transducer operating at a lower center frequency, there is always a tradeoff between depth of penetration and spatial resolution associated with having an ultrasound transducer or ultrasound transducers operating at a center frequency. As IVUS imaging has evolved, there has been a steady migration towards higher ultrasound frequencies to improve the resolution in the display. But as ultrasound frequency is increased, there is diminished contrast between the blood echoes and vessel wall tissue echoes. At the 20 MHz center frequency used in early generations of IVUS, the blood echoes are very weak in comparison to the vessel wall echoes due to the small size of the red blood cell compared to the acoustic wavelength. However, at the 40 MHz ultrasound center frequency now commonly used for IVUS imaging, there is only a modest difference between blood and tissue echoes because the ultrasound wavelength at this higher frequency is closer to the dimensions of the red blood cells. To achieve even greater difference between blood and tissue echoes, an even higher center frequency may be needed. However, such an IVUS device operating at a high center frequency may not be adequate to image the vessel wall tissue as the depth of penetration is being sacrificed.

Conventional solid-state IVUS device has not been amenable to Doppler color flow imaging since the direction of blood flow is predominantly perpendicular to the IUS imaging plane. More specifically, Doppler color flow imaging and other Doppler techniques do not function well when the velocity of interest (i.e., blood flow velocity) is perpendicular to the imaging plane and perpendicular to the direction of ultrasound propagation, resulting in near zero Doppler shift attributable to blood flow.

Thus, while the existing intravascular ultrasound imaging devices are generally acceptable for their general purposes, they are not satisfactory in all aspects. There exists a need for medical imaging devices that includes ultrasound transducers operating at different center frequencies for various purposes.

SUMMARY

Embodiments of the present disclosure provide an improved intravascular ultrasound imaging device for generating images of a blood vessel using transducers operating at different center frequencies. A distal portion of a flexible elongate member of the intravascular imaging device can include an imaging assembly. The imaging assembly can include a first ultrasound transducer operating at a first center frequency and a second ultrasound transducer operating at a second center frequency different from the first center frequency. In some embodiments, the imaging assembly can have a plurality of first ultrasound transducers operating at the first center frequency and a plurality of second ultrasound transducers operating at a second center frequency. The plurality of first and second ultrasound transducers can either form a transducer array annually disposed around a longitudinal axis of the flexible elongate member or disposed linearly parallel to the longitudinal axis of the flexible elongate member.

In one embodiment, an intravascular ultrasound (IVUS) imaging device is provided. The IVUS imaging device includes a flexible elongate member configured to be positioned within a lumen of a patient, the flexible elongate member comprising a proximal portion and a distal portion; and an imaging assembly disposed at the distal portion of the flexible elongate member. The imaging assembly includes a first ultrasound transducer operating at a first center frequency; and a second ultrasound transducer operating at a second center frequency different from the first center frequency.

In some embodiments, the first ultrasound transducer of the IVUS imaging device is one of a plurality of first ultrasound transducers and the second ultrasound transducer of the IVUS imaging device is one of a plurality of second ultrasound transducers. In some embodiments, the plurality of first ultrasound transducers form a first transducer array annularly disposed around a longitudinal axis of the flexible elongate member and the plurality of the second ultrasound transducers form a second transducer array annularly disposed around a longitudinal axis of the flexible elongate member. The first transducer array is positioned proximal to the second transducer array. In some embodiments, the plurality of the first ultrasound transducers form a first transducer array annularly disposed around a longitudinal axis of the flexible elongate member and the plurality of second ultrasound transducers is disposed linearly parallel to the longitudinal axis of the flexible elongate member. In those embodiments, the second center frequency is higher than the first center frequency. In some embodiments, the plurality of first ultrasound transducers form a transducer array annually disposed around a longitudinal axis of the flexible elongate member and each of the plurality of the second ultrasound transducer is interposed between two of the plurality of the first ultrasound transducers.

In some other embodiments, the imaging assembly of the IVUS imaging device is configured to rotate around a longitudinal axis of the flexible elongate member. In those embodiments, the first ultrasound transducer is positioned distally adjacent to the second ultrasound transducer. Further, in those embodiments, the IVUS imaging device further includes a third ultrasound transducer operating at a third center frequency different from the first and second center frequencies, wherein the third ultrasound transducer is positioned proximally adjacent to the second ultrasound transducer. In some implementations, the third ultrasound transducer tilts distally at a first angle. In some instances, the first ultrasound transducer tilts proximally at a second angle.

In one embodiment, an IVUS imaging system is provided. The IVUS imaging system includes a flexible elongate member configured to be positioned within a lumen of a patient, the flexible elongate member comprising a proximal portion and a distal portion; an imaging assembly disposed at the distal portion of the flexible elongate member; and a control and processing device. The imaging assembly includes a first plurality of ultrasound transducers operating at a first center frequency, and a second plurality of ultrasound transducers operating at a second center frequency different from the first center frequency. The control and processing device is in communication with the first plurality of ultrasound transducers and the second plurality of ultrasound transducers. The control and processing device is operable to energize the first plurality of ultrasound transducers to obtain first ultrasound data of the lumen; generate grayscale ultrasound image based on the first ultrasound data; energize the second plurality of ultrasound transducers to obtain second ultrasound data of fluid flowing through the lumen; generate color-Doppler ultrasound images based on the second ultrasound data; and output the grayscale ultrasound images and color-Doppler ultrasound images to a display.

In some embodiments, the first plurality of ultrasound transducers of the imaging assembly forms a first transducer array annularly disposed around a longitudinal axis of the flexible elongate member. In some embodiments, the second plurality of ultrasound transducers of the imaging assembly is disposed linearly parallel to the longitudinal axis of the flexible elongate member. In those embodiments, wherein the second center frequency is higher than the first center frequency. In some embodiments, the control and processing device of the IVUS imaging system is operable to overlay color-Doppler ultrasound images on the grayscale ultrasound images and output to the display the color-Doppler ultrasound images overlaid on the grayscale ultrasound images. In some embodiments, the control and processing device of the IVUS imaging system is operable to energize the second plurality of ultrasound transducers sequentially along the longitudinal axis of the flexible elongate member.

In another embodiment, an IVUS imaging system is provided. The IVUS imaging system includes a flexible elongate member configured to be positioned within a lumen of a patient, the flexible elongate member having a proximal portion and a distal portion; an imaging assembly disposed at the distal portion of the flexible elongate member, the imaging assembly configured to rotate around a longitudinal axis of the flexible elongate member, and a control and processing device. The imaging assembly includes a first ultrasound transducer operating at a first center frequency; and a second ultrasound transducer operating at a second center frequency different from the first center frequency. The control and processing device is in communication with the first ultrasound transducer and the second ultrasound transducer and is operable to energize the first ultrasound transducer to obtain first ultrasound data of the lumen; generate grayscale ultrasound images based on the first ultrasound data; energize the second ultrasound transducer to obtain second ultrasound data of fluid flowing through the lumen; generate color-Doppler ultrasound images based on the second ultrasound data; and output the grayscale ultrasound images and color-Doppler ultrasound images to a display. In some embodiments, the second ultrasound transducer of the imaging assembly is tilted proximally at an angle and the second center frequency is higher than the first center frequency. In some embodiments, the imaging assembly further includes a third ultrasound transducer operating at a third center frequency different from the first and second center frequencies.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
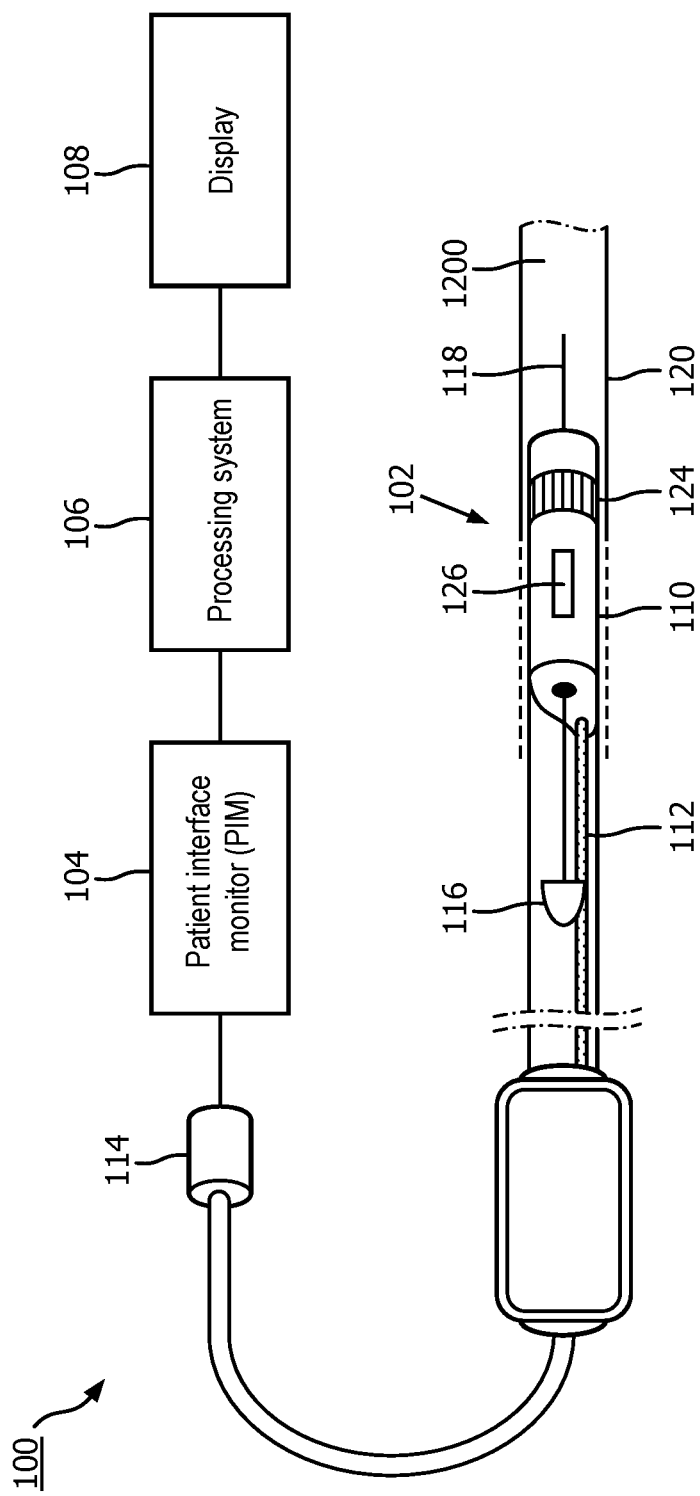
FIG. 1 is a diagrammatic schematic view of a solid-state IVUS imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of a solid-state IVUS imaging system 100, according to aspects of the present disclosure. The IVUS imaging system 100 may include a solid-state IVUS device 102 such as a catheter, guide wire, or guide catheter (sometimes referred to as a flexible elongate member), a patient interface module (PIM) 104, an IVUS processing system or console (sometimes referred to as the control and processing device) 106, and a display 108.

At a high level, the solid-state IVUS device 102 emits ultrasonic energy from a transducer element 124 included in transducer assembly 110 mounted near a distal end of the catheter device. The ultrasonic energy is reflected by tissue structures in the medium, such as a vessel 120, surrounding the transducer assembly 110, and the ultrasound echo signals are received by the transducer element 124. The transducer element 124 can be controlled by a controller(s) 126. For example, the controller(s) 126 can be include electronic circuitry, such as an ASIC. The PIM 104 transfers the received echo signals to the console or computer 106 where the ultrasound image (including the flow information) is reconstructed and displayed on the display 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the transducer assembly 110 included in the solid-state IVUS device 102. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the transducer assembly 110.

The IVUS console 106 receives the echo data from the transducer assembly 110 by way of the PIM 104 and processes the data to reconstruct an image of the tissue structures in the medium surrounding the transducer assembly 110. The console 106 outputs image data such that an image of the vessel 120, such as a cross-sectional image of the vessel 120, is displayed on the display 108. Vessel 120 may represent fluid filled or surrounded structures, both natural and man-made. Vessel 120 defines a lumen 1200. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be an intraluminal imaging device. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the solid-state IVUS device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the transducer assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 in the lumen 1200 through the vessel 120.

Figure 2:
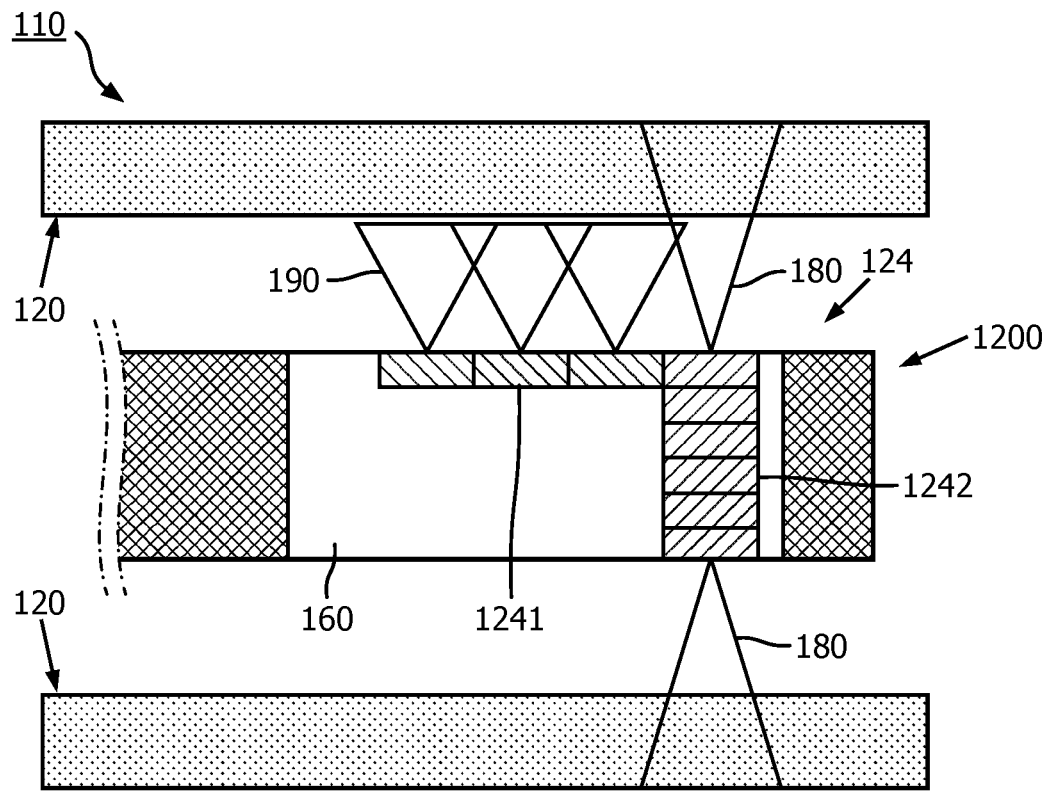
FIG. 2 is a diagrammatic side view of a transducer assembly of a solid-state IVUS imaging system in a lumen of a patient, according to aspects of the present disclosure.

FIG. 2 is a diagrammatic side view of transducer assembly 110 of the solid-state IVUS imaging system 100 in lumen 1200 defined by vessel 120, according to aspects of the present disclosure. The transducer assembly 110 includes transducer element 124 mounted on a flex circuit 160. Various transducer arrangements can be made with the transducer element 124. As shown in FIG. 2, in some embodiment, the transducer element 124 includes a plurality of first ultrasound transducers 1241 and a plurality of second ultrasound transducers 1242. In these embodiments, the first ultrasound transducers 1241 are disposed linearly along a longitudinal axis of the transducer assembly 110. As the transducer assembly 110 shares the same longitudinal axis of the solid-state IVUS imaging device 102 (i.e. flexible elongate member 102), it can be said that the first ultrasound transducers 1241 are disposed linearly parallel to the longitudinal axis of the flexible elongate member 102. In addition, in these embodiments, the second ultrasound transducers 1242 constitute a transducer array annually disposed around the longitudinal axis of the flexible elongate member 102.

In the embodiments represented in FIG. 2, the first ultrasound transducers 1241 operate at a first center frequency and the second ultrasound transducers 1242 operate at a second center frequency. In some instances, the first center frequency is different from the second center frequency. In some other instances, the first center frequency is higher than the second center frequency. In the latter instances, the first ultrasound transducers 1241 with higher first center frequency tend to obtain ultrasound image data featured by a higher spatial resolution but a smaller depth of penetration, while the second ultrasound transducers 1242 with lower second center frequency tend to obtain ultrasound image data characterized by a lower spatial resolution but a greater depth of penetration. As a result, the first ultrasound transducers 1241 have a field of view 190 and the second ultrasound transducers 1242 have a field of view 180. Advantageously, this arrangement allows the transducer array formed of the second ultrasound transducers 1242 to image the vessel 120 with sufficient depth, while allowing the linearly disposed first ultrasound transducers 1241 to image the blood flowing through lumen 1200.

Generally, the center frequencies of the ultrasound transducers can be between 5 MHz and 100 MHz, in various embodiments. For example, the ultrasound transducers can have exemplary center frequencies of 10 MHz, 20 Mhz, 40 MHz, 45 Mhz, 60 MHz, in some embodiments. For example, a single imaging device can include a first ultrasound element with a 10 MHz center frequency, a second ultrasound element with a 20 Mhz center frequency, and a third imaging element with a 60 MHz center frequency, for example. The 10 MHz and 20 MHz center frequencies can advantageously penetrate the vessel wall structure while the 60 Mhz center frequency can advantageously image blood flow.

In addition to different center frequencies, each of the transducer elements can have different parameters associated therewith. The imaging data can be processed to generate IVUS imaging data based on the different parameters. For example, each transducer element can have different gain values corresponding to the different center frequencies. In some instances, the imaging device 102 can include a different controller 126 to control the ultrasound transducers associated with each different center frequency. In some embodiments, the same controller(s) 126 control transducers associated with different center frequencies.

Moreover, the linearly disposed first ultrasound transducers 1241 are capable of obtaining color-Doppler imaging. Although each of the first ultrasound transducers 1241 has a direction of ultrasound propagation perpendicular to the blood flow in lumen 1200, color-Doppler imaging is made possible by energizing each of the first ultrasound transducers 1241 in a manner that generates a non-zero Doppler shift. For example, the first ultrasound transducers 1241 can be energized sequentially (i.e. one by one) in a direction opposite to the direction of blood flow in lumen 1200. This non-zero Doppler shift enables color-Doppler imaging. In some embodiments not shown in FIG. 2, a number of second ultrasound transducers 1242 can be disposed in an alternating fashion with the linearly disposed first ultrasound transducers 1241. That is, a second ultrasound transducer 1242 is interposed between two of the linearly disposed first ultrasound transducers 1241. The alternating linear array of first and second ultrasound transducers 1241 and 1242 can also be energized to generate a non-zero Doppler shift for color-Doppler imaging purposes.

Figure 3:
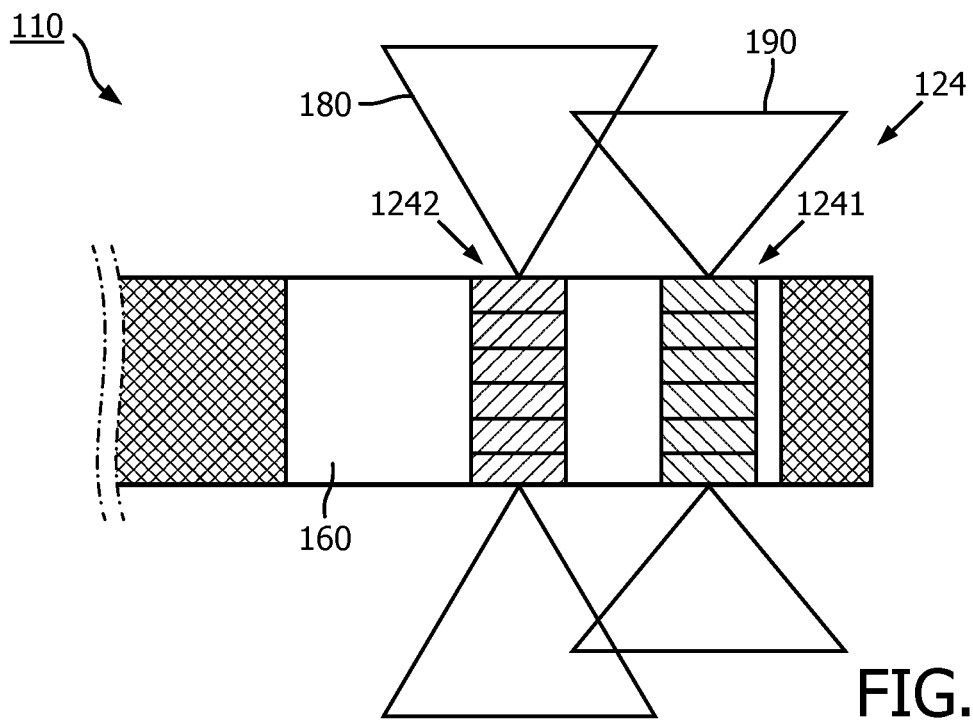
FIG. 3 is a diagrammatic side view of a transducer assembly of a solid-state IVUS imaging system, according to aspects of the present disclosure.

Shown in FIG. 3 is a diagrammatic side view of transducer assembly 110 of the solid-state IVUS imaging system 100, according to aspects of the present disclosure. As shown in FIG. 3, in some embodiments, the first ultrasound transducers 1241 form a first transducer array annually disposed around the longitudinal axis of the transducer assembly 110 and the second ultrasound transducers 1242 form a second transducer array annually disposed around the longitudinal axis of the transducer assembly 110. The first ultrasound transducers 1241 operate at a first center frequency and the second ultrasound transducers operate at a second center frequency. In some instances, the first center frequency is different from the second center frequency. In some other instances, the first center frequency is higher than the second center frequency. In the latter instances, the first ultrasound transducers 1241 with higher first center frequency tend to obtain ultrasound image data featured by a higher spatial resolution but a smaller depth of penetration, while the second ultrasound transducers 1242 with lower second center frequency tend to obtain ultrasound image data characterized by a lower spatial resolution but a greater depth of penetration. As a result, the first ultrasound transducers 1241 have a field of view 190 and the second ultrasound transducers 1242 have a field of view 180.

Figure 4:
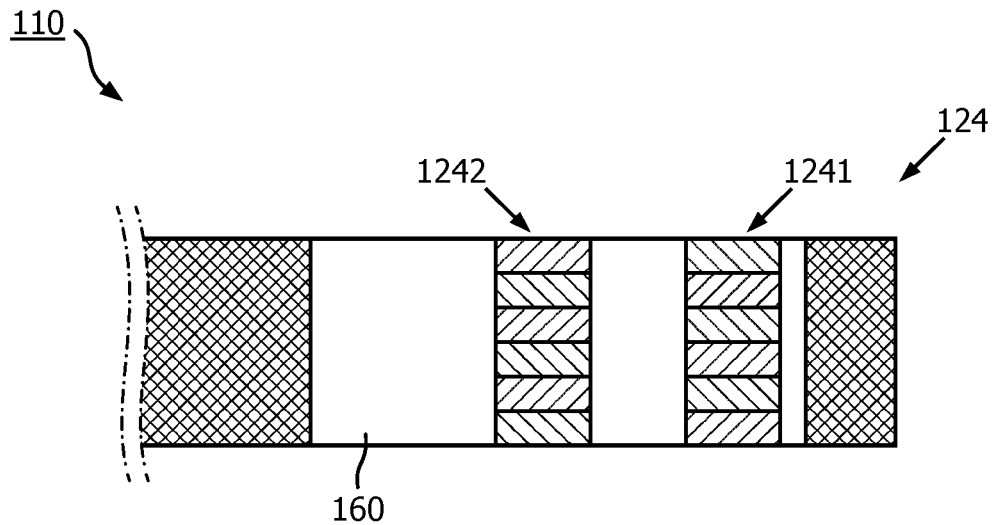
FIG. 4 is a diagrammatic side view of a transducer assembly of a solid-state IVUS imaging system, according to aspects of the present disclosure.

Shown in FIG. 4 is a diagrammatic side view of transducer assembly 110 of the solid-state IVUS imaging system 100, according to aspects of the present disclosure. As shown in FIG. 4, in some embodiments, the first ultrasound transducers 1241 form a transducer array annually disposed around the longitudinal axis of the transducer assembly 110 and each of the second ultrasound transducers 1242 is interposed between two of the first ultrasound transducers 1241. As the first and second ultrasound transducers 1241 and 1242 are interposed, the reverse is true. It can be said that the second ultrasound transducers 1242 form a transducer array annually disposed around the longitudinal axis of the transducer assembly 110 and each of the first ultrasound transducers 1241 is interposed between two of the second ultrasound transducers 1242. The resultant transducer array can be referred to as an alternating transducer array. The first ultrasound transducers 1241 operate at a first center frequency and the second ultrasound transducers operate at a second center frequency. In some instances, the first center frequency is different from the second center frequency. In some implementation, the transducer element 124 may include two or more of alternating transducer array.

With respect to the types of transducers, in an embodiment, the first and second ultrasound transducers 1241 and 1242 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the first and second ultrasound transducers 1241 and 1242 are piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof. In some implementations, the first ultrasound transducers 1241 are of a type of transducers while the second ultrasound transducers 1242 are of a different type. For example, in some instances, the first ultrasound transducers 1241 are CMUTs and the second ultrasound transducers 1242 are PMUTs.

The flex circuit 160, on which the first and second ultrasound transducers 1241 and 1242 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). The thickness of the film layer of the flex circuit 160 is generally related to the degree of curvature in the final assembled transducer assembly 110. In some embodiments, the film layer is between 5 µm and 100 µm, with some particular embodiments being between 12.7 µm and 25.1 µm.

Reference is now made to FIG. 1 and the operation of the solid-state IVUS imaging system 100 is described. The transmission line bundle or cable 112 include a plurality of conductors that are coupled to the first and second ultrasound transducers 1241 and 1242. In some embodiments, the transducers 1241, 1242 are formed on the flexible substrate 160. In other embodiments, the transducer 1241 and/or transducers 1242 are disposed separate substrates. In some instances, to reduce the requisite number of conductors, the solid-state IVUS imaging system 100 can include a micro-beam-former integrated circuit (IC) to control transducer arrays formed of first and second ultrasound transducers 1241 and 1242. The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104, which is coupled to the IVUS console 106. The IVUS console 106 is operable to energize the first and second ultrasound transducers 1241 and 1242, separately, simultaneously or sequentially. The IVUS console 106 is also operable to receive the echo data (sometimes referred to as ultrasound data) from the transducer assembly 110 by way of the PIM 104 and processes the data to reconstruct an image of the tissue structures in the medium surrounding the transducer assembly 110. For example, in embodiments represented by FIG. 2, the IVUS console 106 is operable to energize the linearly disposed first ultrasound transducers 1241 and receive the ultrasound data perceived by the linearly disposed first ultrasound transducers 1241. The IVUS console 106 is then operable to generate color-Doppler ultrasound images based on such ultrasound data. In addition, the IVUS console 106 is also operable to energize the annually disposed second ultrasound transducers 1242 and receive the ultrasound data perceived by the second ultrasound transducers 1242. The IVUS console 106 can then generate gray scale ultrasound images based on the ultrasound data perceived by the second ultrasound transducers 1242. Furthermore, the IVUS console 106 is operable to output the color-Doppler ultrasound images and grayscale ultrasound images to the display 108. In some instances, the IVUS console 106 is operable to overlay the color-Doppler ultrasound images on grayscale ultrasound images and output the color-Doppler ultrasound images overlaid on the grayscale ultrasound images. In some instances, the IVUS console 106 is operable to receive the imaging data obtained by the multiple imaging elements operating at different center frequencies and reconstruct a 3D IVUS image of the vessel.

Figure 5:
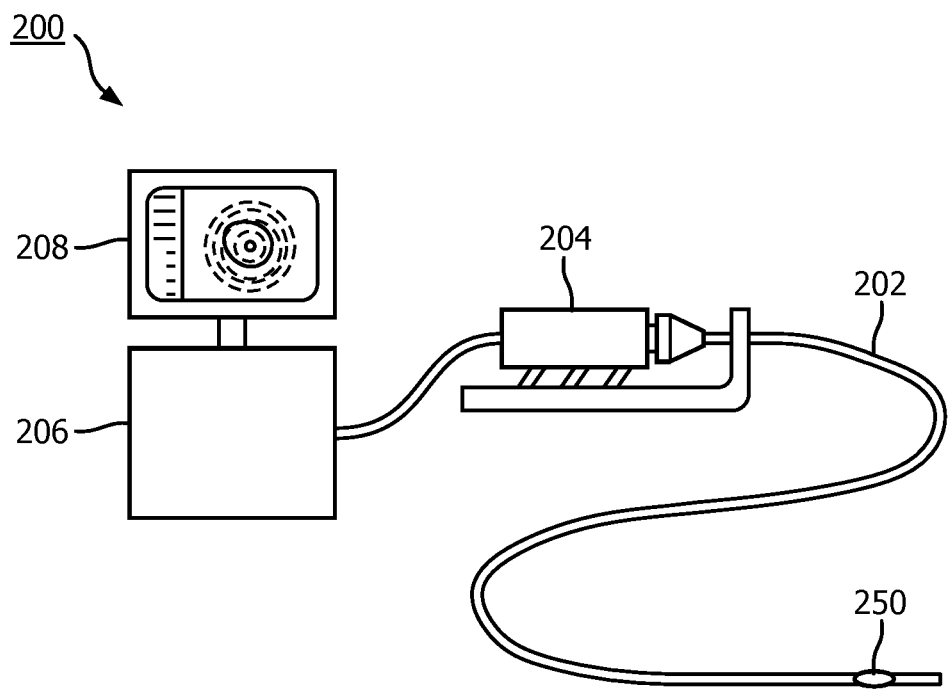
FIG. 5 is a diagrammatic schematic view of a rotation IVUS imaging system, according to aspects of the present disclosure.

FIG. 5 shows an IVUS imaging system 200 according to an embodiment of the present disclosure. In some embodiments of the present disclosure, the IVUS imaging system 200 is a rotational IVUS imaging system. In that regard, the main components of the rotational IVUS imaging system are a rotational IVUS catheter 202, a patient interface module (PIM) 204, an IVUS console or processing system 206 (sometimes referred to control and processing device), and a monitor 208 to display the IVUS images generated by the IVUS console 206. Catheter 202 includes an ultrasound element 250 in some embodiments. As will be described with more details below, ultrasound element 250 may include more than one ultrasound transducers. PIM 204 implements the appropriate interface specifications to support catheter 202. According to some embodiments, PIM 204 generates a sequence of transmit trigger signals and control waveforms to regulate the operation of ultrasound element 250.

Ultrasound element 250 transmits ultrasound signals substantially perpendicular to the longitudinal axis of the catheter into the vessel lumen and outward towards the vessel wall. The ultrasound emission from the transducer is activated by a corresponding electrical signal received from PIM 204. Ultrasound element 250 also converts ultrasound echo signals from the vessel tissue (and other reflectors) into electrical signals that are communicated to PIM 204.

Figure 6:
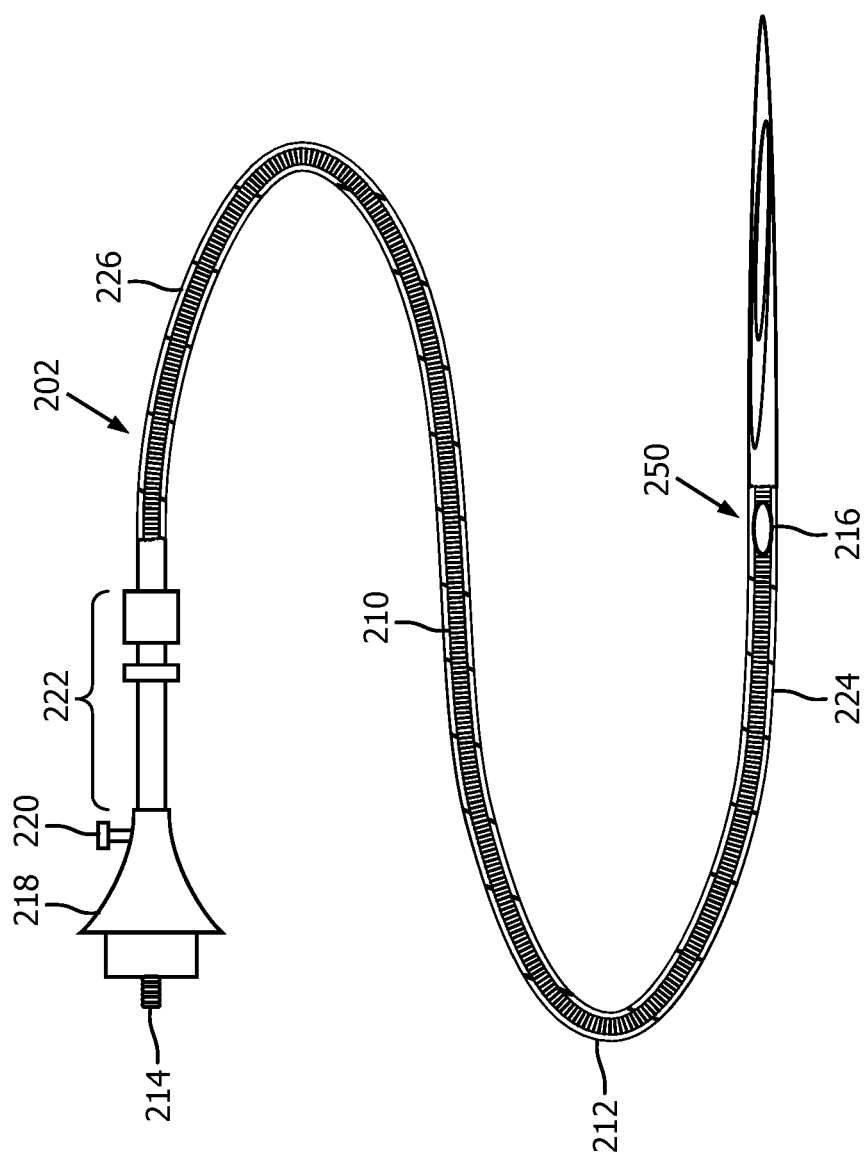
FIG. 6 is a diagrammatic, partial cutaway perspective view of a rotational IVUS imaging device, according to aspects of the present disclosure.

FIG. 6 shows a diagrammatic, partial cutaway perspective view of catheter 202, according to an embodiment of the present disclosure. FIG. 2 shows additional detail regarding rotational IVUS catheter 202. Rotational catheter 202 includes an imaging core 210 and an outer catheter/sheath assembly. Imaging core 210 includes a flexible drive shaft that is terminated at the proximal end by a rotational interface 214 providing electrical and mechanical coupling to PIM 204 (cf. FIG. 1). The distal end of the flexible drive shaft of the imaging core 210 is coupled to a transducer assembly 216 containing ultrasound element 250.

Catheter/sheath assembly 212 (sometimes referred to as flexible elongate member 212) includes a hub 218 supporting rotational interface 214 and provides a bearing surface and a fluid seal between rotating and non-rotating elements of catheter 202. In some embodiments, hub 218 includes a luer lock flush port 220 through which saline is injected to flush out the air and fill the inner lumen of the sheath with an ultrasound-compatible fluid at the time of use of the catheter. Saline or other similar fluid is required, since ultrasound frequencies are highly attenuated by air, and strongly reflected at any air-solid or air-liquid interface. Saline also provides a biocompatible lubricant for the rotating driveshaft. In some implementations, hub 218 is coupled to a telescope 222 that includes nested tubular elements and a sliding fluid seal that permits catheter/sheath assembly 212 to be lengthened or shortened. Telescope 222 facilitates axial movement of the transducer housing within an acoustically transparent window 224 at the distal portion of catheter/sheath assembly 212.

In some embodiments, window 224 is composed of thin-walled plastic tubing fabricated from material(s) that readily conduct ultrasound waves between the transducer and the vessel tissue with minimal attenuation, reflection, or refraction. A proximal shaft 226 of catheter/sheath assembly 212 bridges the segment between telescope 222 and window 224. In some embodiments, proximal shaft 226 is composed of a material or composite that provides a lubricious internal lumen and optimum stiffness to catheter 202. In some embodiments, the catheter/sheath assembly 212 and/or the window 224 includes features as described in U.S. Provisional Patent Application No. 61/746,958, titled "INTRA-VASCULAR ULTRASOUND CATHETER FOR MINIMIZING IMAGE DISTORTION, filed Dec. 28, 2012, which is hereby incorporated by reference in its entirety.

Figure 7:
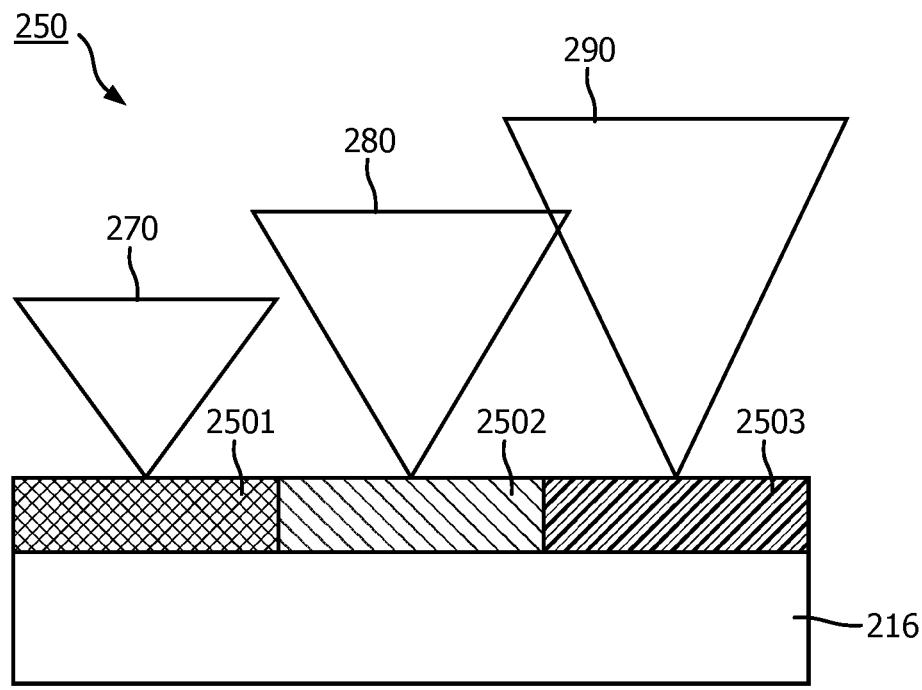
FIG. 7 is a diagrammatic side view of a transducer assembly of a rotational IVUS imaging system, according to aspects of the present disclosure.
Figure 8:
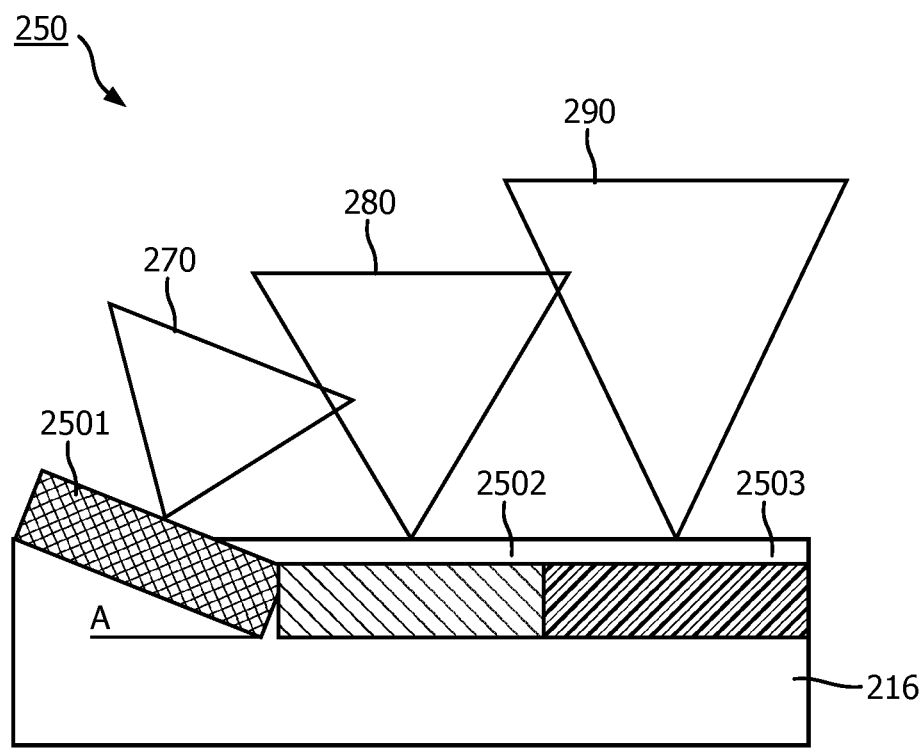
FIG. 8 is a diagrammatic side view of a transducer element of a rotational IVUS imaging system, according to aspects of the present disclosure.
Figure 9:
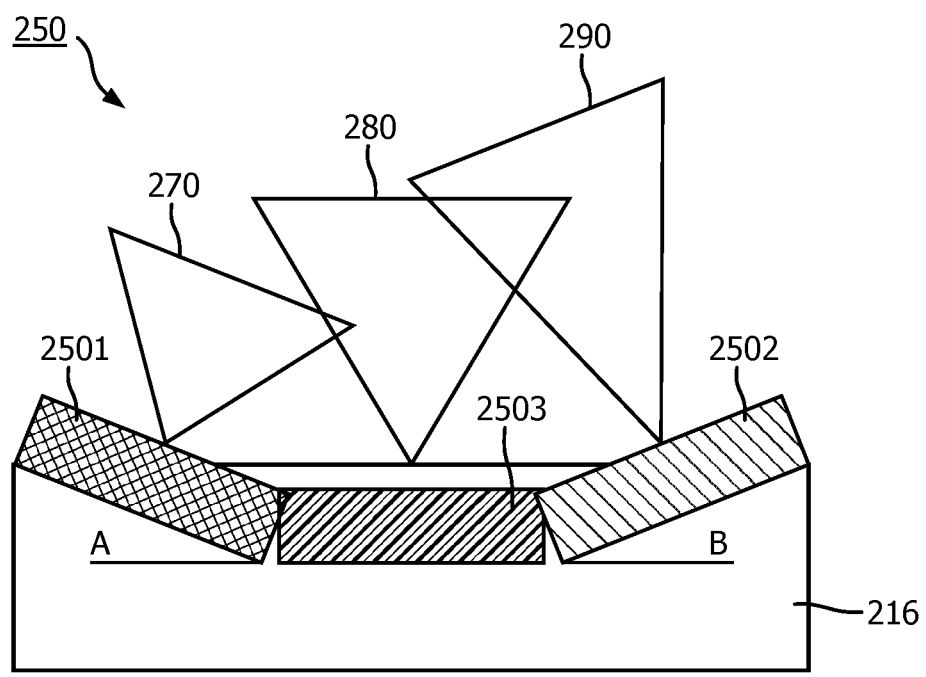
FIG. 9 is a diagrammatic side view of a transducer element of a rotational IVUS imaging system, according to aspects of the present disclosure.

FIGS. 7, 8 and 9 are diagrammatic side views of transducer element 250 of rotational IVUS imaging system 200 with various transducer arrangements, according to aspects of the present disclosure. As shown in FIG. 7, in some embodiments, the transducer element 250 includes a first ultrasound transducer 2501 operating at a first center frequency, a second ultrasound transducer 2502 operating at a second center frequency, and a third ultrasound transducer 2503 operating at a third center frequency. In some implementations, the first, second and third ultrasound transducers 2501, 2502 and 2503 are disposed linearly parallel to a longitudinal axis of the transducer element 250. As the transducer element 250 shares the same longitudinal axis of the flexible elongate member 212, it can be said the first, second and third ultrasound transducers 2501, 2502 and 2503 are disposed linearly parallel to the longitudinal axis of the flexible elongate member 212. In some instances, the first, second and third center frequencies are different from one another. In other instances, the first center frequency is higher than the second center frequency, and the second center frequency is higher than the third center frequency. In those instances, the first ultrasound transducer 2501 has highest spatial resolution and a smallest depth of penetration of the three ultrasound transducers. The third ultrasound transducer 2503 has the smallest spatial resolution and a greatest depth of penetration of the three, while the second ultrasound transducer 2502 has mid pack spatial resolution and depth of penetration. As a result, the first ultrasound transducer 2501 has a field of view 270, the second ultrasound transducer 2502 has a field of view 280, and the third ultrasound transducer 2503 has a field of view 290.

FIG. 8 shows an arrangement of ultrasound transducers 2501, 2502 and 2503 different from what is shown in FIG. 7. As shown in FIG. 7, in some embodiments, the first ultrasound transducer 2501 does not lay flat in the transducer assembly 216 but is tilted at an angle A. It is noted that the first ultrasound transducer 2501 can be tilted distally or proximally. In some instances, the tilted first ultrasound transducer 2501 operates at the highest center frequency. In some implementations, the second center frequency is higher than the third center frequency. As a result, in FIG. 9, the first ultrasound transducer 2501 has a field of view 270, the second ultrasound transducer 2502 has a field of view 280, and the third ultrasound transducer 2503 has a field of view 290.

In the embodiment pictured in FIG. 8, the IVUS console or processing system 206 can be configured to acquire Doppler ultrasound data from a blood vessel from the first ultrasound transducer 2501, and can analyze the data to determine the presence or absence, the direction, and the amount of fluid flow. Doppler ultrasound measures the movement of objects through the emitted beam as a phase change in the received signal. When ultrasound waves are reflected from a moving structure (e.g., a red blood cell within a blood vessel), the wavelength and the frequency of the returning waves are shifted. If the moving structure is moving toward the first ultrasound transducer 2501, the frequency increases. If the moving structure is moving away from the first ultrasound transducer 2501, the frequency decreases.

In some embodiments, the IVUS console or processing system 206 can employ the Doppler Equation:

$$\Delta f = (2 f_0 V \cos \theta)/C$$

where $\Delta f$ is the frequency shift, $f_0$ is the frequency of the transmitted wave, V is the velocity of the reflecting object (e.g., a red blood cell), $\theta$ is the angle between the incident wave and the direction of the movement of the reflecting object (i.e., the angle of incidence), and C is the velocity of sound in the medium. The frequency shift is maximal if the first ultrasound transducer 2501 is oriented parallel to the direction of the blood flow and the $\theta$ is zero degrees (cos 0=1). The frequency shift is absent if the transducer 130 is oriented perpendicular to the direction of the blood flow and the $\theta$ is 90 degrees (cos 90=0). Higher Doppler frequency shifts are obtained when the velocity is increased, the incident wave is more aligned to the direction of blood flow, and/or if a higher frequency is emitted.

FIG. 9 shows an arrangement of ultrasound transducers 2501, 2502 and 2503 different from what is shown in FIGS. 7 and 8. As shown in FIG. 9, in some embodiments, both the first ultrasound transducer 2501 and the second ultrasound transducer 2502 do not lay flat in the transducer assembly 216 but are tilted at angles A and B, respectively. In some embodiments, the first and second ultrasound transducers 2501 and 2502 are tilted towards the center. That is, one of the first and second ultrasound transducers 2501 and 2502 is tilted distally while the other is tilted proximally. As long as the sound wave propagating from the first and second ultrasound transducers 2501 and 2502 includes elements parallel to the blood flow, both of them can be used to obtain ultrasound imaging data to generate color-Doppler images. In the embodiment shown in FIG. 9, the third ultrasound transducer 2503 has a lowest center frequency is disposed between the first and second ultrasound transducers 2501 and 2502 along the longitudinal axis of the flexible elongate member 212. As a result, in FIG. 9, the first ultrasound transducer 2501 has a field of view 270, the second ultrasound transducer 2502 has a field of view 280, and the third ultrasound transducer 2503 has a field of view 290. The fields of view 270, 280, and 290 can be overlapping in some instances. In that regard, a computing device can generate a single IVUS image of a single location of the vessel using data from multiple transducers (with different center frequencies).

Figure 10:
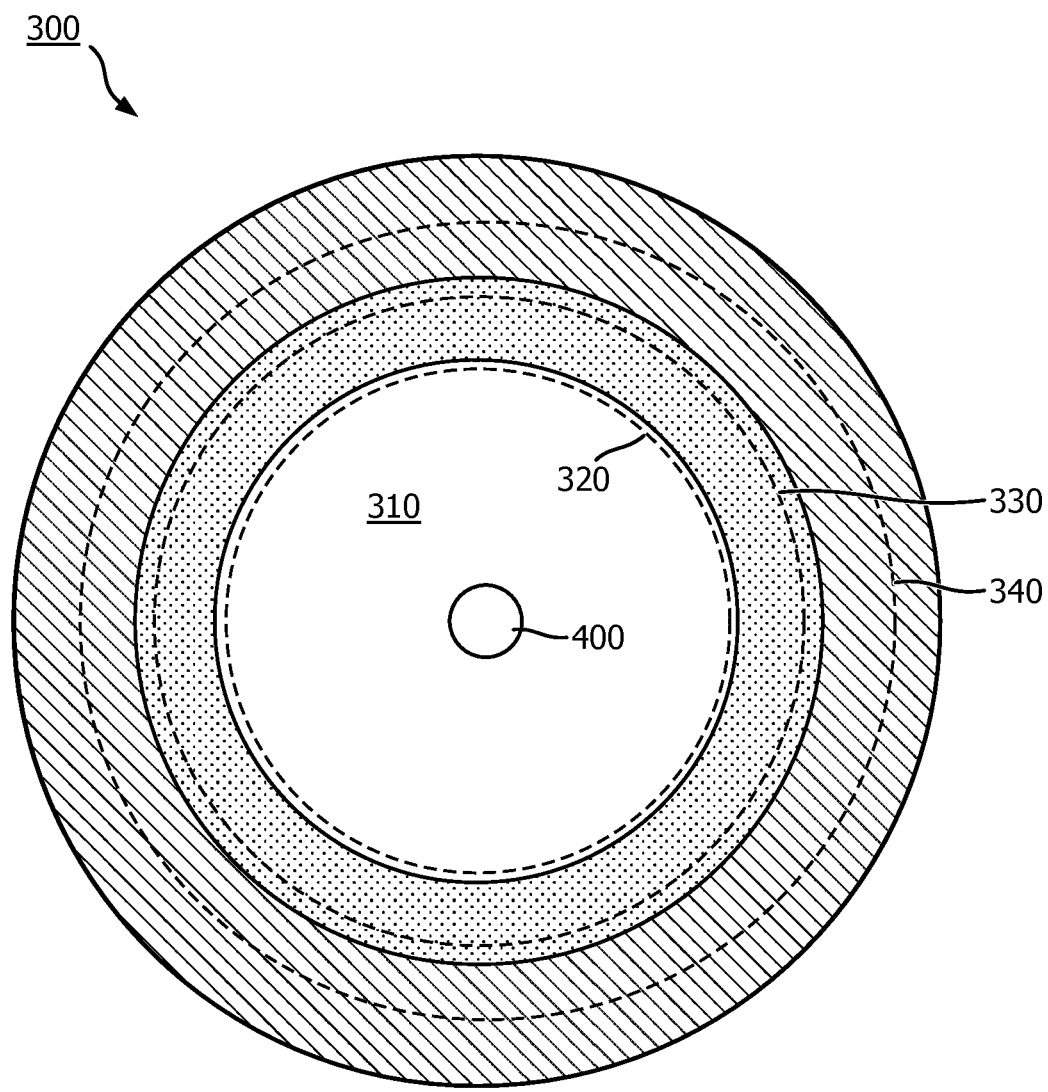
FIG. 10 is a cross-section view of a vessel of a patient, according to aspects of the present disclosure.

FIG. 10 is a cross-section view of a vessel 300 of a patient, according to aspects of the present disclosure. Vessel 300 includes several layers. For example, vessel 300 includes tunica intima 330 and tunica media 340. Tunica intima 330 has an internal vessel wall 320, which defines a lumen 310. When an IVUS device 400, such as IVUS device 102 or catheter 202, is positioned with the lumen 310, it is advantageous if the IVUS device 400 is capable of obtaining ultrasound imaging data of differing depth of penetration to resolve features in tunica intima 330, the tunica media 340, and velocity of blood flowing in lumen 310. Advantageously, the present disclosure provides IVUS imaging systems that include multiple ultrasound transducers operating at different center frequencies. With use of IVUS imaging systems disclosed in the present disclosure, a physician performing catheterization can obtain not only grayscale ultrasound images but also color-Doppler images without having to insert different purpose-built IVUS catheters into a patient's vessel.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound imaging device (IVUS imaging device) comprising:
a flexible elongate member configured to be positioned within a lumen of a patient, the flexible elongate member comprising a proximal portion and a distal portion;
an imaging assembly disposed at the distal portion of the flexible elongate member, the imaging assembly including:
a first transducer array comprising a plurality of first ultrasound transducers disposed annularly around a longitudinal axis of the flexible elongate member and operating at a first center frequency; and
a second transducer array comprising a plurality of second ultrasound transducers disposed parallel to the longitudinal axis of the flexible elongate member and operating at a second center frequency different from the first center frequency.

2. The IVUS imaging device of claim 1, wherein the second center frequency is higher than the first center frequency.

3. An intravascular ultrasound imaging device (IVUS imaging device) comprising:
a flexible elongate member configured to be positioned within a lumen of a patient, the flexible elongate member comprising a proximal portion and a distal portion;
an imaging assembly disposed at the distal portion of the flexible elongate member, the imaging assembly including:
a first transducer array comprising a plurality of first ultrasound transducers disposed annularly around a longitudinal axis of the flexible elongate member and operating at a first center frequency; and
a second transducer array comprising a plurality of second ultrasound transducers disposed parallel to the longitudinal axis of the flexible elongate member and operating at a second center frequency different from the first center frequency and wherein each of the plurality of the second ultrasound transducers is interposed between two of the plurality of the first ultrasound transducers.

4. The IVUS imaging device of claim 1, wherein the imaging assembly is configured to rotate around a longitudinal axis of the flexible elongate member.

5. The IVUS imaging device of claim 4, wherein the first transducer array is positioned distally adjacent to the second transducer array.

6. The IVUS imaging device of claim 5, further comprising a third ultrasound transducer operating at a third center frequency different from the first and second center frequencies, wherein the third ultrasound transducer is positioned proximally adjacent to the second ultrasound transducer.

7. The IVUS imaging device of claim 6, wherein the third ultrasound transducer tilts distally at a first angle.

8. The IVUS imaging device of claim 7, wherein the first ultrasound transducer tilts proximally at a second angle.

9. An intravascular ultrasound imaging system (IVUS imaging system), comprising:
a flexible elongate member configured to be positioned within a lumen of a patient, the flexible elongate member comprising a proximal portion and a distal portion;
an imaging assembly disposed at the distal portion of the flexible elongate member, the imaging assembly including:
a first transducer array comprising a first plurality of ultrasound transducers annularly disposed around a longitudinal axis of the flexible elongate member and operating at a first center frequency; and
a second transducer array comprising a second plurality of ultrasound transducers disposed linearly parallel to the longitudinal axis of the flexible elongate member and operating at a second center frequency different from the first center frequency;
a control and processing device in communication with the first plurality of ultrasound transducers and the second plurality of ultrasound transducers, the control and processing device operable to:
energize the first plurality of ultrasound transducers to obtain first ultrasound data of the lumen;
generate grayscale ultrasound image based on the first ultrasound data;
energize the second plurality of ultrasound transducers to obtain second ultrasound data of fluid flowing through the lumen;
generate color-Doppler ultrasound images based on the second ultrasound data; and
output the grayscale ultrasound images and color-Doppler ultrasound images to a display.

10. The IVUS imaging system of claim 9, wherein the second center frequency is higher than the first center frequency.

11. The IVUS imaging system of claim 9, wherein the control and processing device is operable to overlay color-Doppler ultrasound images on the grayscale ultrasound images and output to the display the color-Doppler ultrasound images overlaid on the grayscale ultrasound images.

12. The IVUS imaging system of claim 9, wherein the control and processing device is operable to energize the second plurality of ultrasound transducers sequentially along the longitudinal axis of the flexible elongate member.

* * * * *